US008298573B2

(12) United States Patent
Zhang et al.

(10) Patent No.: US 8,298,573 B2
(45) Date of Patent: Oct. 30, 2012

(54) STABLE STERILE FILTERABLE LIPOSOMAL ENCAPSULATED TAXANE AND OTHER ANTINEOPLASTIC DRUGS

(76) Inventors: Jia-Ai Zhang, Vernon Hills, IL (US); Sydney Ugwu, Wheeling, IL (US); Lan Ma, Gurnee, IL (US); Gopal Anyarambhatla, Waukegan, IL (US); Imran Ahmad, Wadsworth, IL (US)

(*) Notice: Subject to any disclaimer, the term of this patent is extended or adjusted under 35 U.S.C. 154(b) by 815 days.

(21) Appl. No.: 11/196,123

(22) Filed: Aug. 3, 2005

(65) Prior Publication Data

US 2006/0029658 A1    Feb. 9, 2006

Related U.S. Application Data

(63) Continuation of application No. PCT/US2004/003157, filed on Feb. 3, 2004.

(60) Provisional application No. 60/444,958, filed on Feb. 3, 2003.

(51) Int. Cl.
*A61K 9/127* (2006.01)
*A61K 31/335* (2006.01)

(52) U.S. Cl. .................... 424/450; 514/449
(58) Field of Classification Search .................. None
See application file for complete search history.

(56) References Cited

U.S. PATENT DOCUMENTS

| 4,534,899 A | 8/1985 | Sears |
| 4,861,580 A | 8/1989 | Janoff et al. |
| 4,880,635 A * | 11/1989 | Janoff et al. ............... 424/450 |
| 4,898,735 A | 2/1990 | Barenholz et al. |
| 4,927,571 A | 5/1990 | Huang et al. |
| 4,952,408 A | 8/1990 | Rahman |
| 4,960,790 A | 10/1990 | Stella et al. |
| 5,041,278 A | 8/1991 | Janoff et al. |
| 5,059,591 A | 10/1991 | Janoff et al. |
| 5,094,854 A | 3/1992 | Ogawa et al. |
| 5,234,634 A | 8/1993 | Janoff et al. |
| 5,330,689 A | 7/1994 | Janoff et al. |
| 5,415,869 A | 5/1995 | Straubinger et al. |
| 5,424,073 A | 6/1995 | Rahman et al. |
| 5,534,499 A | 7/1996 | Ansell |
| 5,554,382 A | 9/1996 | Castor |
| 5,565,478 A | 10/1996 | Kohn et al. |
| 5,621,001 A | 4/1997 | Canetta et al. |
| 5,641,803 A | 6/1997 | Carretta et al. |
| 5,648,090 A | 7/1997 | Rahman et al. |
| 5,665,761 A | 9/1997 | Canetta et al. |

(Continued)

FOREIGN PATENT DOCUMENTS

CA    2132711 A1    9/1993

(Continued)

OTHER PUBLICATIONS

Litzinger et al., Biochim Biophys Acta, 1994, 1190(1), pp. 99-107.*

(Continued)

*Primary Examiner* — Brian Gulledge
(74) *Attorney, Agent, or Firm* — Wood, Phillips, Katz, Clark & Mortimer

(57) ABSTRACT

The invention provides a formulation of one or more antineoplastic drugs encapsulated in liposomes including at least a lipid fraction in addition to the antineoplastic drug, wherein the composition is stable in an aqueous solution at room temperature.

39 Claims, 2 Drawing Sheets

U.S. PATENT DOCUMENTS

| | | | |
|---|---|---|---|
| 5,670,537 A | 9/1997 | Canetta et al. | |
| 5,683,715 A * | 11/1997 | Boni et al. | 424/450 |
| 5,693,336 A * | 12/1997 | Moynihan | 424/450 |
| 5,696,153 A | 12/1997 | Ainsworth et al. | |
| 5,756,537 A | 5/1998 | Gill | |
| 5,919,816 A | 7/1999 | Hausheer et al. | |
| 5,994,409 A | 11/1999 | Stogniew et al. | |
| 6,066,331 A | 5/2000 | Barenholz et al. | |
| 6,090,955 A | 7/2000 | Reszka et al. | |
| 6,118,011 A | 9/2000 | Mayhew et al. | |
| 6,146,659 A | 11/2000 | Rahman | |
| 6,461,637 B1 | 10/2002 | Rahman | |

FOREIGN PATENT DOCUMENTS

| | | | |
|---|---|---|---|
| CA | 2153326 A1 | | 5/1995 |
| CA | 2294981 A1 | | 1/1999 |
| EP | 0750910 A1 | | 1/1997 |
| EP | 0750910 A1 | | 2/1997 |
| HU | 217839 B | | 1/1993 |
| HU | P9903952 A | | 9/1997 |
| JP | 6-329533 A | | 11/1994 |
| JP | 8-034745 A | | 2/1996 |
| JP | 8-508046 A | | 8/1996 |
| JP | 9-315978 A | | 12/1997 |
| WO | WO 82/03769 A1 | | 11/1982 |
| WO | WO 88/09168 A1 | | 12/1988 |
| WO | WO 93/18751 A1 | | 9/1993 |
| WO | WO 95/13053 A1 | | 5/1995 |
| WO | WO 96/15774 A1 | | 5/1996 |
| WO | WO 96/21658 A1 | | 7/1996 |
| WO | WO 97/10234 A1 | | 3/1997 |
| WO | WO 00/01366 | * | 1/2000 |
| WO | WO 00/01366 A1 | | 1/2000 |

OTHER PUBLICATIONS

Sharma et al., *Pharmaceutical Research*, 11(6), 889-896 (Jun. 1994).
Agata et al., "Anti-Tumor Activity of Docetaxel in Non-small Cell Lung Cancer Xenografts is Potentiated by NM-3, an Angiogenesis Inhibitor," *ILEX Products, Inc.*, Abstract No. 2752.
U.S. Appl. No. 10/266,030, filed Oct. 7, 2002, Rahman.
Ali et al., "Hydrolyzable Hydrophobic Taxanes: Synthesis and Anti-Cancer Activities," *Anti-Cancer Drugs*, 12, 117-128 (2001).
Bonadonna, *Annals of Oncology*, 3, 417-418 (1992).
Brown et al., "A phase I trial of Taxol given by a 6-hour intravenous infusion," *J. Clin. Oncol.*, 9 (7), 1261-1267 (Jul. 1991).
Devries, *Annals of Oncology*, 3, 419-421 (1992).
Donehower et al., "Phase I trial of Taxol in patients with advanced cancer," *Cancer Treat. Rep.*, 71 (12), 1171-1177 (Dec. 1987).
Eisenhauer et al., "European-Canadian randomized trial of paclitaxel in relapsed ovarian cancer: High-dose versus low-dose and long versus short infusion," *J. Clin. Oncol.*, 12 (12), 2654-2666 (Dec. 1994).
Essayan et al., "Successful Parenteral Desensitization to Paclitaxel," *J. Allergy Clin. Immunol.*, 97(1), 42-46 (1996).
Gelderblom et al., "Influence of Cremophor EL on the Bioavailability of Intraperitoneal Paclitaxel," *Clinical Cancer Research*, 8, 1237-1241 (2002).
Gianni et al., "Nonlinear pharmacokinetics and metabolism of paclitaxel and its pharmacokinetic/pharmacodynamic relationships in humans," *J. Clin. Oncol.*, 13 (1), 180-190 (Jan. 1995).
Henningsson et al., "Mechanism-Based Pharmacokinetic Model for Paclitaxel," *J. Clin. Oncol.*, 19(20), 4065-4073 (2001).
Hoeprich, "Clinical Use of Amphotericin B and Derivatives: Lore, Mystique and Fact," *Clinical Infectious Disease*, 14(Suppl 1), S114-S119 (1992).
Holton et al., "Oral Anti-Tumor Activity of TL00139 (MAC-321) A New Taxane," *Annual Meeting of the American Association for Cancer Research*, Abstact No. 2732, (2003).
Huizing et al., "Pharmacokinetics of paclitaxel and metabolites in a randomized comparative study in platinum-pretreated ovarian cancer patients," *J. Clin. Oncol.*, 11 (11), 2127-2135 (Nov. 1993).
Johnson, "Taxol," *Physicians' Desk Reference*, PDR 54th Eds., 881-887 (2000).
Longley et al., "In Vitro Mechanism of Action Studies With the Taxane Analog—TL00139 (MAC-321)," *Annual Meeting of the American Association for Cancer Research*, Abstact No. 2733, (2003).
Marty et al., "A Comparison of Docetaxel and Paclitaxel Against Adult Human Solid Tumor Xenografts in Nude Mice," *IDD*, Abstract No. 2757 (2003).
Onyuksel et al., *Pharmaceutical Research*, 11(2), 206-212 (1994).
Ostro, American Journal Hosp. Pharm., 46, 1576-1587 (1989).
Petit et al., "In-vivo therapeutic efficacy in experimental murine mycoses of a new formulation of deoxycholate-amphotericin B obtained by mild heating," *J. Antimicrob. Chemother.*, 42, 779-785 (1998).
Rahman et al., Cancer Chemother. Pharmacol., 16, 22-27 (1986).
Rahman et al., Cancer Research, 42, 1817-1825 (1982).
Rahman et al., Chemical Abstracts, Abstract No. 104(102092), (Mar. 31, 1986).
Riondel et al., In Vivo, 6, 23-27 (1992).
Romanelli et al., "In vitro and in vivo interaction between cisplatin and topotecan in ovarian carcinoma systems," *Cancer Chemother Pharmacol.*, 41, 385-390 (1998).
Rosa, Transplant Biochem. Model Syn. Res., 243-256 (1982).
Sparreboom et al., "Cremophor EL-mediated Alteration of Paclitaxel Distribution in Human Blood: Clinical Pharmacokinetic Implications," *Cancer Research*, 59, 1454-1457 (1999).
Sparreboom et al., "Introduction: Recent Topics in the Clinical Pharmacology of Taxanes that Might Change Future Perspectives," *Invest. New Drugs*, 19, 111-112 (2001).
Sparreboom et al., "Preclinical Pharmacokinetics of Paclitaxel and Docetaxel," *Anti-Cancer Drug*, 9, 1-17 (1998).
Sparreboom et al., "Tissue Distribution, Metabolism and Excretion of Paclitaxel in Mice," *Anti-Cancer Drugs*, 7, 78-86 (1996).
Weinstein, "Liposomes in the diagnosis and treatment of cancer," in *Liposomes From Biophysics to Therapeutics* (Ostro, ed.), 277-338 (Marcel Dekker, Inc., New York, NY, 1987).
Zuylen et al., "Role of Formulation Vehicles in Taxane Pharmacology," *Invest. New Drugs*, 19, 125-141 (2001).
Office Action dated Jun. 15, 2004 in U.S. Appl. No. 10/239,598.
Office Action dated Dec. 22, 2004 in U.S. Appl. No. 10/239,598.
Office Action dated May 24, 2005 in U.S. Appl. No. 10/239,598.
Office Action dated Apr. 20, 2006 in U.S. Appl. No. 10/239,598.
Office Action dated Dec. 8, 2003 in U.S. Appl. No. 10/266,030.
Office Action dated Oct. 1, 2004 in U.S. Appl. No. 10/266,030.
Office Action dated Jan. 26, 2005 in U.S. Appl. No. 10/266,030.
Office Action dated Apr. 4, 2005 in U.S. Appl. No. 10/266,030.
Office Action dated Oct. 27, 2005 in U.S. Appl. No. 10/266,030.
Brown et al., "A phase I trial of Taxol given by a 6-hour intravenous infusion," *J Clin. Oncol.*, 9 (7), 1261-1267 (Jul. 1991).
Eisenhauer et al., "European-Canadian randomized trial of paclitaxel in relapsed ovarian cancer: High-dose versus low-dose and long versus short infusion," *J Clin. Oncol.*, 12 (12), 2654-2666 (Dec. 1994).
Rahman et al., Cancer Chemother. Phamiacol., 16, 22-27 (1986).

* cited by examiner

STABLE STERILE FILTERABLE LIPOSOMAL ENCAPSULATED TAXANE AND OTHER ANTINEOPLASTIC DRUGS

CROSS-REFERENCE TO RELATED APPLICATIONS

This application is a continuation of PCT/US04/03157, filed on Feb. 3, 2004, which claims priority to U.S. Provisional Patent Application 60/444,958, filed on Feb. 3, 2003. The disclosures of these applications are incorporated herein in their entireties by reference thereto.

TECHNICAL FIELD OF THE INVENTION

The present invention relates to liposomal encapsulated taxane and other antineoplastic drugs.

BACKGROUND OF THE INVENTION

The use of taxanes, such as paclitaxel, as anti-tumor agents for patients suffering from diseases, such as ovarian and breast cancer, is known. In addition, paclitaxel has been shown to be clinically potent as a synergistic agent when used in conjunction with radiation treatment. Paclitaxel has a unique mechanism of action and a broad spectrum of anticancer activity because paclitaxel shows stabilization of microtubules rather than disassembly of microtubules.

However, paclitaxel has extremely low solubility in water, which makes it difficult to provide a suitable dosage form. Currently, paclitaxel is prepared and administered in a vehicle containing 6 mg/mL paclitaxel, 527 mg/mL of purified cremophor EL (a polyethoxylated castor oil), and 49.7% dehydrated alcohol, USP. This solution is diluted 1:10 in saline before being administered to humans. The stability of paclitaxel once diluted in saline solution is quite low. The drug degrades within 24 hours, and it has been shown that taxol is incompatible with common PVC intravenous bag and infusion sets, thus, handling of dosage for the patients becomes very difficult. Since the drug precipitates from dilution, an on-line filter is utilized for the infusion of the drug to the patients. The decreased solubility and presence of Cremophor EL in the formulations presents risks to patients, such as anaphylactoid reactions and cardiotoxicity. The long-term use of taxol also can contribute to the development of multidrug resistance in cancer cells, which only complicates the etiology of the very disease for which taxol treatment is sought.

Attempts have been made to improve upon the currently-available formulations of taxol. To this end, U.S. Pat. No. 5,648,090 (Rahman et al.) and U.S. Pat. No. 5,424,073 (Rahman et al.) provide a liposomal encapsulated paclitaxel for a method for treating cancer in mammals using such a liposomal-encapsulated paclitaxel, or antineoplastic derivative thereof. The '090 and '073 patents disclose a method of modulating multidrug resistance in cancer cells in a mammalian host by administering to the host a pharmaceutical composition of a therapeutically effective number of liposomes, which include a liposome-forming material, cardiolipin, and an agent such as paclitaxel, or an antineoplastic derivative of paclitaxel, or a mixture thereof, and a pharmaceutically acceptable excipient. However, there remains a need for a liposomal formulation of taxanes that remain stable for a prolonged period of time.

SUMMARY OF THE INVENTION

The present invention provides a formulation of antineoplastic drugs, such as taxanes, derivatives thereof, and related compounds, at clinically relevant concentrations that exhibit improved stability and reduced toxicity. The inventive formulation preferably contains one or more stabilizing agents, antioxidants, and lyoprotectants. In many preparations, the inventive formulation is stable for many days at room temperature, even after post-reconstitution and dilution in injectable fluids. The inventive formulation can increase therapeutic efficacy and minimize multidrug resistance over that observed with present taxane formulations. These and other advantages of the present invention, as well as additional inventive features, will be apparent from the description of the invention provided herein and from the accompanying figures.

DETAILED DESCRIPTION OF THE INVENTION

Figure 1:
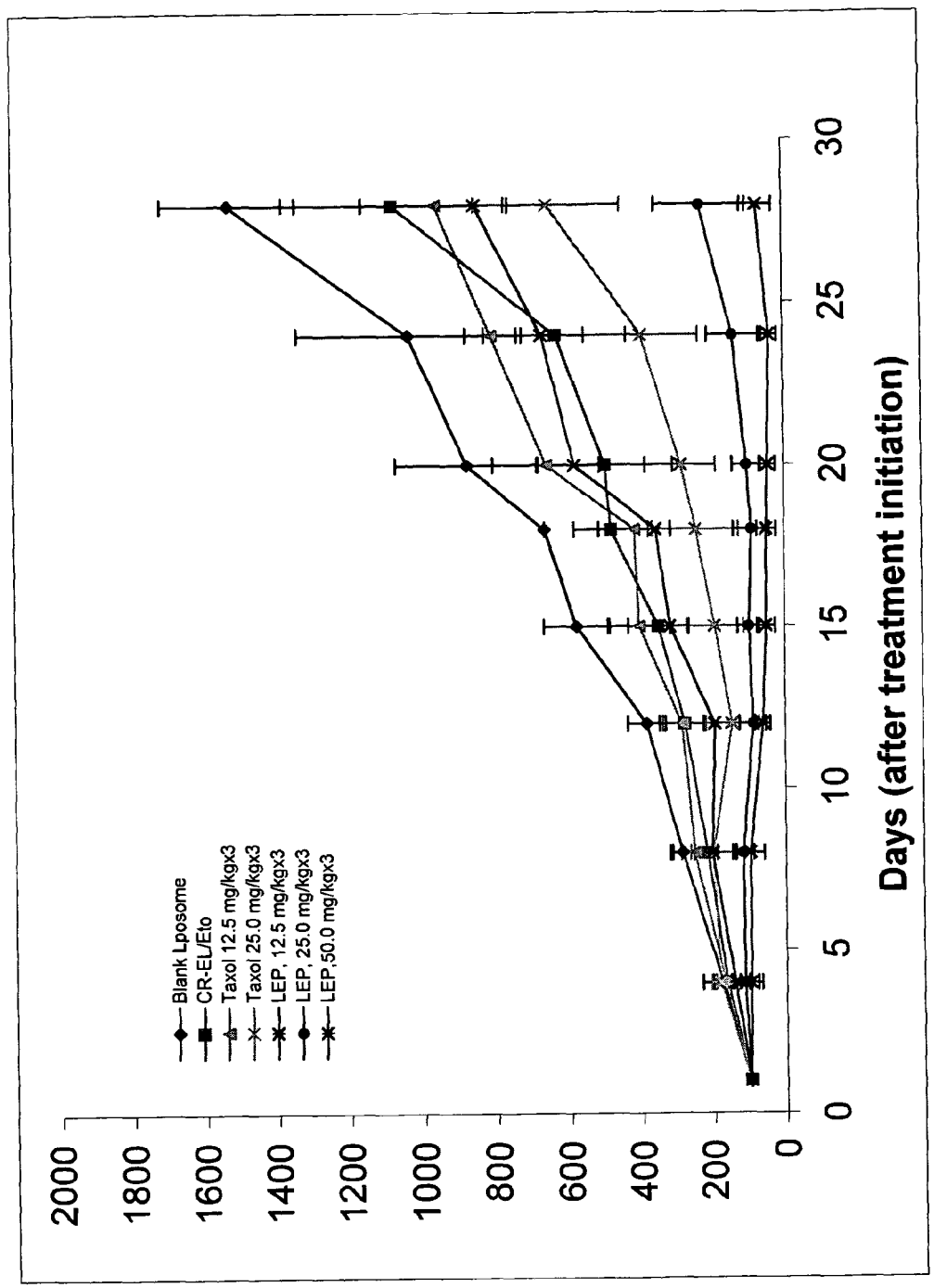
FIG. 1 graphically presents the results of a study of the effect of liposome entrapped paclitaxel (LEP) and Taxol on growth of ectopic human lung tumor (A549) in SCID mice.

The present invention is predicated, at least in part, on providing a formulation of one or more antineoplastic drugs encapsulated in liposomes including at least a lipid fraction in addition to the antineoplastic drug, wherein the composition is stable in an aqueous solution at room temperature, typically stable for at least 3 days. Preferably, the formulation is free or substantially free of antineoplastic drug crystals or precipitate, and most preferably, there are no antineoplastic drug crystal and precipitate forms in the formulation.

Any suitable antineoplastic drug can be used in the context of the invention. Preferred compounds for use in the inventive formulation include taxanes or derivatives, such as docetaxel, paclitaxel and related compounds (e.g., epothilones A and B, epothilone derivatives, etc.). Preferably, the compound is paclitaxel. A suitable derivative of paclitaxel is taxane. Other suitable compounds are 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, taxotere, and mixtures thereof.

As the invention provides a liposomal formulation of antineoplastic drug, the formulation also includes one or more compounds able to form liposomes. Thus, for example, the formulation can include cholesterol or derivatives thereof, lipids or phospholipids, and other similar compounds. Preferably, the lipid fraction of the inventive liposomal formulation includes one or more cardiolipins, such as synthetic or naturally occurring cardiolipins or cardiolipin analogues.

Typically, the lipid fraction comprises at least about 3.5% (w/v) and more preferably at least about 4.0% (w/v) of the inventive composition, such as at least about 5.0% or even at least about 5.5% (w/v) of the composition. Generally, it is not expected that the lipid fraction will exceed about 8.5% (w/v), and more preferably, the maximal lipid fraction will be about 8.0% (w/v) of the composition, such as a top lipid concentration of about 7.0% (w/v) or even a maximal lipid concentration of about 6.0% (w/v). Preferably, the liposomes of the inventive formulation will have between about 4.0% (w/v) and about 8.0% (w/v) lipid, such as between about 5.0% (w/v) and about 6.0% (w/v) lipid.

Moreover, the ratio of lipid to antineoplastic drug used in the inventive formulation typically is at least about 5:1 by molar ratio, and more preferably at least about 10:1 by molar ratio, at least where the antineoplastic drug is a taxane (or related compound or derivative thereof). Typically, the ratio of lipid to antineoplastic drug used in the inventive formulations is at least about 20:1 by molar ratio, such as at least about 30:1 or even 40:1 by ratio. However, generally, the ratio of lipid to antineoplastic drug used in the inventive formulation generally does not exceed about 75:1 by molar ratio, and is more typically at most about 70:1 by molar ratio. Typically, the ratio of lipid to antineoplastic drug, especially a taxane (or related compound or derivative) used in the inventive formulations is at most about 60:1 by molar ratio, such as at most about 50:1 or even at most about 40:1 by molar ratio. Preferably, the ratio of lipid to drug in the inventive formulation is between about 10:1 and about 70:1 by molar ratio, such as between about 25:1 and about 55:1 by molar ratio.

Desirably, a majority of the antineoplastic drug in the formulation is entrapped in the liposomes. More preferably, at least about two-thirds (such as at least about 75%) of the antineoplastic drug in the formulation is entrapped in the liposomes, and it is even more preferable for at least about 85% (or even more than about 90%) of the antineoplastic drug to be entrapped in the liposomes in the inventive formulation.

Preferably the lipid fraction of the formulation includes one or more lipids selected from the group consisting of 1,2-dioleoyl-sn-glycero-3-phosphocholine (DOPC), tetramyristoyl cardiolipin (CL), and cholesterol (CH), as these constituents lend stability to the formulation and can function as stabilizing agents. Other saturated phospholipids such as dimyristolphosphatidylcholine (DMPC), dipalmitoylphosphatidylcholine (DPPC) and distearoylphasphatidylcholine (DSPC) and unsaturated phospholipids such as hydrogenated purified soy bean phosphatidylcholine, hydrogenated purified egg yolk phosphatidylcholine, dilinoleoylphosphatidylcholine (DLPC), phosphatidylcholine (DOPC), palmitoyloleoyl dioleoylphosphatidylcholine (POPC) and sphingomyelin may be used. Suitable negatively charged lipids such as dioleoylphsophatidylglycerol (DOPG), dioleoyl phosphatidylserine (DOPS), dimyristolphosphatidylglycerol (DMPG) also can be used.

Most preferred constituents for inclusion in the lipid fraction of the inventive composition include 1,2-dioleoyl-sn-glycero-3-phosphocholine (DOPC), tetramyristoyl cardiolipin (CL), and cholesterol (CH). It is desirable for two or more of these lipid constituents to be present in the lipid fraction, and most preferably all three of these lipid constituents (DOPC, CL, and CH) are present. Indeed, the DOPC preferably comprises between about 85% and about 95% of the lipid components, and even more preferably between about 90% and about 92% of the lipid components. Suitable formulations include ratios of DOPC:CH:CL between about 92:0:8 to about 90:5:5, although the amounts of CH and CL do not have to be equal. In this respect, the concentration of CH typically is between about 0.3 mg/ml and about 3.5 mg/ml, such as between about 0.5 mg/ml and about 3.0 mg/ml, or even between about 1 mg/ml and about 2 mg/ml; whereas the amount of CL typically is between about 1 mg/ml and about 10 mg/ml (more typically between about 2 mg/ml and about 8 mg/ml), such as about 5 mg/ml. However, the amount of DOPC in the lipid fraction of the inventive formulation generally exceeds that of CH or CL, and typically the amount of DOPC in the inventive formulation exceeds the amount of both CH and CL combined. In this respect, the amount of DOPC in the lipid fraction of the inventive formulation typically is about 60 mg/ml, and is generally at least about 40 mg/ml, such as at least about 45 mg/ml or even at least about 50 mg/ml. Typically, the DOPC represents no greater than about 75 mg/ml, such as at most about 65 mg/ml or 70 mg/ml. An ideal range of DOPC is between about 44 mg/ml and about 74 mg/ml.

To further assist in enhancing the stability, the inventive formulation can typically include one or more antioxidants, in addition to the active drug (e.g., taxane or related compounds) and the lipid fraction. While any commonly-used lipid soluble antioxidants can be employed, in some embodiments, antioxidants such as butylated hydroxyanisole, butylated hydroxytoulene and propyl gallate may be used. D-alpha tocopheryl acid succinate is preferred because of its stability-enhancing properties. Where present, the antioxidant typically is included in the formulation in concentrations between about 0.1 and about 0.6 mg/ml, such as between about 0.2 mg/ml and between about 0.5 mg/ml, or even between about 0.3 mg/ml and about 0.4 mg/ml.

The liposomes can be formulated by any suitable method. Preferred methods include thin film hydration, solvent injection, freeze-thawing and dehydration-rehydration, removal of surfactant, reverse phase evaporation and ethanol injection. For example, the antineoplastic drug and lipid fraction can be dissolved in a suitable solvent, such as methylene chloride, ethanol, methyl acetate, ethyl formate and the like. Where antioxidants are employed, they also can be dissolved in the solvent with the lipid fraction. For the purpose of formulating the inventive composition, any suitable amount of solvent can be employed, which typically is between about 1000 and 1100 mg/ml where methylene chloride is used as the solvent. Typically, however, the method will require at least about 500 mg/ml methylene chloride, such as least about 750 mg/ml mg/ml methylene chloride, and as much as about 2000 mg/ml methylene chloride, such as up to about 1500 mg/ml methylene chloride can be used to dissolve the lipid fraction.

After the antineoplastic drug, lipid fraction, and antioxidant are dissolved in the solvent, the solution then is dried. Any suitable drying methodology and apparatus can be employed, a preferred drying step comprising a rotary evaporator under reduced pressure, followed by further drying in a dessicator.

Following drying, the lipid (and antioxidant) residue can be hydrated in an aqueous system, such as water, which can be a solution or suspension. Preferably, the solution contains one or more lyoprotectants to aid in enhancing the stability of the formulation during subsequent lyophilization and while present in lyophilized form. Any suitable lyoprotectant, such as sugars and mannitol can be employed, although such compounds typically are sugars. While sucrose is a most preferred lyoprotetant, other suitable lyoprotectants include, for example, trehalose, maltose, lactose, glucose, dextran, aminoglycosides and streptomycin and combinations of these can suitably be employed, as desired. Typically, the lyoprotectant represents less than about 50% (w/v) of the formulation, if it is employed. More typically, the lyoprotectant represents at most about 40% (w/v) of the formulation, such as at most about 30% (w/v) of the formulation. Where the lyoprotectant represents as little as about 1% (w/v), it can enhance the stability of the inventive formulations; however, more typically, the lyoprotectant represents at least about 5% (w/v) of the formulation, such as at least about 10% (w/v) or at least about 20% (w/v) of the formulation. The hydration solution also can contain a tonicity adjuster, which preferably is sodium chloride (NaCl), but can be another suitable salt or disaccharide. The hydration can be accomplished in any suitable volume of hydration solution.

Re-hydration in the hydration solution results in the formation of multilamellar vesicles (MLV). In certain methods, suitable preparations can be mixtures of multilamellar vesicles and unilamellar vesicles. Once the solution is added, liposomes can be formed by mixing, for example, as by vortexing or by using any suitable mixing devise. Where smaller vesicles are desirable, the solution can be sonicated. If desired, the size of these MLV can be manipulated, for example, by extrusion through a sieve, which is typically formed of polycarbonate fibers or by homogenization using high pressure homogenizer. Thus, the size of the MLV in the composition can be controlled, using a sieve of a pre-selected size (e.g., via extrusion through a sieve of a desired size, such as 0.81 μm, 0.4 μm, 0.2 μm, 0.1 μm, etc.). In the present invention, a sizing treatment is preferably applied to make the particle size of the drug-encapsulating liposomes more uniform. Prior to lyophilization, the formulations of the present invention can be sterile filtered through a 0.22 micron filter. The average particle size of the formulation is about 50 to 200 nm, preferably 100-180 nm, more preferably 120-160 nm.

Following re-hydration and (if desired) extrusion to achieve a defined particle size, the composition preferably is lyophilized using any suitable device or method. A preferred device is a benchtop and any suitable size of lyophilizer (e.g., such as is manufactured by VerTis). The SUV preparation can be maintained in lyophilized form (e.g., in cold storage at about −5-8° C.) for an extended period of time, such as for at least about several months or years. Preferably the lyophilized formulation is stable for at least 9 months.

For use, the lyophilized SUV liposomal formulation can be reconstituted with a suitable volume of reconstitution solution, more preferably is a polar solvent, and most preferably an aqueous system, which can be deionized water or a suitable aqueous saline solution. Any suitable volume of reconstitution solution can be employed, such as between about 1 ml and about 50 ml, more typically between about 3 ml and about 25 ml. For use, the liposomal formulation can be diluted as desired, such as in a suitable physiologically-compatible buffer or saline solution. To assist in reconstitution, the preparation can be mixed gently or vigorously (e.g., vortexed) as desired, or even sonicated.

However produced, the resultant liposomal-encapsulated taxane is stable for at least about one day, and more typically for at least 3 or 4 days following re-constitution. Indeed, formulations of the present invention can remain stable at room temperature for at least about 4 days, such as a week or two weeks, or even longer times. As indicated below in the Example sections, formulations of the present invention can remain stable under such conditions for at least about 17 days. Stability can be monitored, for example, by assessing the particle size of the liposomes over time (stability in this context can be indicated by a change of mean particle size of less than about 20% over one day and more preferably a change of particle size of less than about 5% in one day, or a change of less than about 10% or even 5% over a 3- or 4-day timecourse) using particle size analyzer, such as Nicomp Submicron Particle Sizer. Alternatively, stability can be assessed by assessing (e.g., using a light microscope) for the presence of crystalline taxane. The absence of more than trace amounts of such crystals is indicative of a stable preparation, and desirably, the inventive formulation will remain substantially, or even relatively completely, free of taxane crystals after three or four days of reconstitution or dilution in saline, even at room temperature.

The present liposomal formulations provide a drug-delivery system which allows infusion of high concentrations of taxanes or other antineoplastic drugs in a stable form and which provides sustained therapeutic benefits at target sites, while maintaining low concentrations of insoluble free taxane and minimal adverse toxic effects than were previously known.

The present pharmaceutical composition can be administered in amounts of at least 50 to 400 mg of active compound/$m^2$ of mammalian host surface area, within a period of less than about three hours, preferably in less than about two hours, and most preferably 90 minutes without causing a substantial toxic reaction. For example, in a 70 kg human, about 0.5 to 7.0 mg active compound per kg of body weight can be safely administered in about 90 minutes. Preferably, about 1.0-5.0 mg of active compound per kg of body weight is administered. Alternatively, preferable amounts include 75, 135, 175, 250, 300, 325, and 375 mg/$m^2$.

The present liposome compositions can be administered intravenously or intraperitoneally to an isolated portion of a mammalian body, particularly a human body, such as an arm or leg, or in the case of a human, a hand, or can be injected directly into a tumor. Preferably the formulations of the present invention can be in injectable form.

Liposomal encapsulated taxane has a substantial beneficial effect in overcoming multidrug resistance in cancer cells, which are subjected to chemotherapy. By using the liposomal composition of the present invention, it is possible to reduce the tendency of cancer cells subjected to chemotherapy to develop resistance to the chemotherapeutic agents used for chemotherapy such as anthracycline glycosides. This method includes administering to a host a pharmaceutical composition of a liposomal encapsulated taxane of the present invention in accordance with the administration protocol.

Taxanes and the anti-neoplastic derivatives thereof may be used to treat any form of mammalian cancer. Such compounds are thought to function by promoting the assembly of microtubules or prohibiting the tubulin disassembly process. Taxane and the anti-neoplastic derivatives thereof are of particular advantageous use in the treatment of mammalian lymphoma, ovarian, breast, lung and colon cancer, and particularly those conditions in humans.

The following examples further illustrate the present invention but, of course, should not be construed as in any way limiting its scope.

EXAMPLE 1

This example demonstrates the construction of a liposomal encapsulated taxane formulation of the present invention. The following ingredients were employed in the amounts as indicated in Table 1:

TABLE 1

| Ingredients | Concentration | Concentration |
| --- | --- | --- |
| Taxane | 2.0 mg (paclitaxel) | 4.0 mg (docetaxel) |
| 1,2-Dioleoyl-sn-Glycero-3-Phosphocholine (DOPC) | 54.2 mg | 57.2 |
| Tetramyristoyl Cardiolipin (CL) | 4.9 mg | 5.2 mg |
| Cholesterol (CH) | 1.48 mg | 1.6 mg |
| D-Alpha Tocopheryl acid Succinate | 0.31 mg | 0.31 mg |
| Sucrose | 100 mg | 200 mg |
| Sodium Chloride (NaCl) | 9.0 mg | 9.0 mg |
| Methylene Chloride, USP* | 1130 mg | — |
| Dehydrate alcohol, USP* | — | 158 mg |
| Water for Injection QS. AD. | 1.0 ml | 1.0 ml |

*To be removed during evaporation and lyophilization processes.

The lipids (DOPC, 1,2-dimyristoyl cardiolipin, cholesterol and D-Alpha Tocopheryl acid Succinate) and paclitaxel or docetaxel were dissolved in either methylene chloride or dehydrate alcohol. The lipid solution then was evaporated to dryness using a rotary evaporator under vacuum. After evaporation, the lipid residue was further dried overnight in a dessicator. The sucrose and NaCl were dissolved in de-ionized water to achieve the required batch concentrations. Then, the dried lipid residue was hydrated in the sucrose/NaCl solution to form multi-lamellar vesicles (MLV). The size of the MLV was further reduced in size by extrusion through 0.8 μm, 0.4 μm, 0.2 μm, and 0.1 μm sized polycarbonate filters. Five millimeters of the final formulation was filled into glass vials and freeze-dried using a benchtop VIRTIS Lyophilizer.

EXAMPLE 2

This example demonstrates the construction of a liposomal encapsulated taxane formulation of the present invention. The following ingredients were employed in the amounts as indicated in Table 2:

TABLE 2

| Ingredients | Concentration | Concentration |
| --- | --- | --- |
| Taxane | 2.0 mg (paclitaxel) | 6.0 mg (docetaxel) |
| 1,2-Dioleoyl-sn-Glycero-3-Phosphocholine (DOPC) | 53 mg | 78 mg |
| Tetramyristoyl Cardiolipin (CL) | 7.5 mg | 8.4 mg |
| Cholesterol (CH) | — | 10.2 mg |
| D-Alpha Tocopheryl acid Succinate | 0.43 mg | 0.31 mg |
| Sucrose | 100 mg | 200 mg |
| NaCl | 9.0 mg | 2.5 mg |
| Methylene Chloride, USP* | 1068 mg | — |
| Dehydrate alcohol, USP* | — | 158 |
| Water for Injection QS. AD. | 1.0 ml | 1.0 ml |

*To be removed during evaporation and lyophilization processes.

This formulation was manufactured as indicated in Example 1.

EXAMPLE 3

This example demonstrates the construction of a liposomal encapsulated taxane formulation of the present invention. The following ingredients were employed in the amounts as indicated in Table 3:

TABLE 3

| Ingredients | Concentration | Concentration |
| --- | --- | --- |
| Taxane | 2.0 mg (paclitaxel) | 4.0 mg (docetaxel) |
| 1,2-Dioleoyl-sn-Glycero-3-Phosphocholine (DOPC) | 54.2 mg | 57.2 mg |
| Tetramyristoyl Cardiolipin (CL) | 4.9 mg | 5.2 mg |
| Cholesterol (CH) | 1.5 mg | 1.6 mg |
| D-Alpha Tocopheryl acid Succinate | 0.31 mg | 0.31 mg |
| Sucrose | 200 mg | 200 mg |
| Nacl | 9.0 mg | 9.0 mg |
| Dehydrate alcohol, USP* | 200 mg | 158 mg |
| Water for Injection QS. AD. | 1 ml | 1.0 ml |

*To be removed during evaporation and lyophilization processes

This formulation was manufactured as indicated in Example 1.

EXAMPLE 4

This example demonstrates the properties of the formulation manufactured in accordance with Example 1.

The lyophilized vials were reconstituted with 4.5 mL of deionized water. After complete reconstitution, the liposomes were further diluted 1:8 in normal saline or deionized water. The liposome vesicle size of the reconstituted and diluted formulations was measured by dynamic light scattering technique (Nicomp Submicron Particle Sizer) over a 17-37 day period, wherein the reconstituted formulations were maintained at room temperature. The reconstituted and diluted formulations also were examined for presence of paclitaxel and docetaxel crystals using an optical microscope (DMIL Microscope).

The results of these measurements made from the paclitaxel and docetaxel formulations prior to lyophilization are presented in Table 4 and 5:

TABLE 4

Physical Stability of Liposomal Paclitaxel Formulation

| Time | | Particle Size (nm) | | Optical Microscopic |
| --- | --- | --- | --- | --- |
| (Days) | Condition | Mean | 99 Percentile< | Observations |
| Initial | | 113 | 189 | No crystals |
| 1 | 2-8° C. | 115 | 185 | No crystals |
| 2 | 2-8° C. | 114 | 188 | No crystals |
| 3 | 2-8° C. | 101 | 167 | No crystals |
| 4 | 2-8° C. | 112 | 179 | No crystals |
| 7 | 2-8° C. | 108 | 182 | No crystals |
| 17 | 2-8° C. | 105 | 181 | No crystals |

TABLE 5

Physical Stability of Liposomal Docetaxel Formulation

| Time | | Particle Size (nm) | | Optical Microscopic |
| --- | --- | --- | --- | --- |
| (Days) | Condition | Mean | 99 Percentile< | Observations |
| Initial | | 106 | 179 | No crystals |
| 2 | 2-8° C. | 108 | 188 | No crystals |
| 5 | 2-8° C. | 106 | 173 | No crystals |
| 9 | 2-8° C. | 106 | 177 | No crystals |
| 12 | 2-8° C. | 107 | 180 | No crystals |
| 16 | 2-8° C. | 106 | 156 | No crystals |
| 37 | 2-8° C. | 106 | 175 | No crystals |

The results of these measurements made from the paclitaxel and docetaxel formulations of Example 1 after lyophilization and reconstitution are presented in Table 6 and 7:

TABLE 6

Physical Stability of Liposomal Paclitaxel Formulation after lyophilization and reconstitution

| Time | | Particle Size (nm) | | Optical Microscopic |
| --- | --- | --- | --- | --- |
| (Days) | Condition | Mean | 99 Percentile< | Observations |
| Initial | Room temp. | 134 | 283 | No crystals |
| 1 | Room temp. | 133 | 253 | No crystals |
| 3 | Room temp. | 131 | 260 | No crystals |
| 4 | Room temp. | 132 | 272 | No crystals |

The measurements made from the paclitaxel formulation of Example 1 after dilution (1:8 in normal saline) are set forth in Table 7:

TABLE 7

| Time | | Particle Size (nm) | | Optical Microscopic |
|---|---|---|---|---|
| (Days) | Condition | Mean | 99 Percentile< | Observations |
| Initial | Room temp. | 134 | 268 | No crystals |
| 1 | Room temp. | 135 | 259 | No crystals |
| 3 | Room temp. | 133 | 261 | No crystals |
| 4 | Room temp. | 131 | 273 | No crystals |

The measurements made from the docetaxel formulation of Example 1 after dilution (1:8 in normal saline) are set forth in Table 8:

TABLE 8

| Time after dilution | | Particle size (nm) | | Optical Microscopic |
|---|---|---|---|---|
| (Hours) | Condition | Mean | 99 Percentile< | Observations |
| Before dilution | | 112 | 196 | No crystals |
| 0 | | 115 | 206 | No crystals |
| 6 | RT | 116 | 208 | No crystals |
| 24 | RT | 115 | 196 | No crystals |

EXAMPLE 4

This example demonstrates the properties of the formulation manufactured in accordance with Example 2. The methodology is the same as that described in Example 3, and the measurements made from the paclitaxel and docetaxel formulation prior to lyophilization are set forth in Table 9 and 10:

TABLE 9

| Time | | Particle Size (nm) | |
|---|---|---|---|
| (Days) | Condition | Mean | 99 Percentile< |
| Initial | Room temp. | — | — |
| 1 | Room temp. | 109 | 175 |
| 2 | Room temp. | 109 | 185 |
| 3 | Room temp. | 112 | 172 |
| 4 | Room temp. | 111 | 165 |

TABLE 10

Physical stability of liposomal docetaxel formulation prior to lyophilization

| Time | | Particle Size (nm) | | Optical Microscopic |
|---|---|---|---|---|
| (Days) | Condition | Mean | 99 Percentile< | Observations |
| Initial | | 112 | 183 | No crystals |
| 2 | 2-8° C. | 113 | 194 | No crystals |
| 5 | 2-8° C. | 113 | 200 | No crystals |

The results of these measurements made from the formulations of Example 2 after lyophilization and reconstitution are presented in Table 11 and 12:

TABLE 11

| Time | | Particle Size (nm) | | Optical Microscopic |
|---|---|---|---|---|
| (Days) | Condition | Mean | 99 Percentile< | Observations |
| Initial | Room temp. | 148 | 317 | No crystals |
| 1 | Room temp. | 142 | 308 | No crystals |
| 2 | Room temp. | 146 | 310 | No crystals |
| 3 | Room temp. | 142 | 293 | No crystals |
| 4 | Room temp. | 144 | 314 | NA |

TABLE 12

Physical stability of liposomal docetaxel formulation after lyophilization and reconstitution

| Time after reconstitution | | Particle Size(nm) | | Optical Microscopic |
|---|---|---|---|---|
| (Hours) | Condition | Mean | 99 Percentile< | Observations |
| Before lyo | | 124 | 208 | No crystals |
| 0 | | 129 | 275 | No crystals |
| 4 | RT | 136 | 280 | No crystals |
| 7 | RT | 135 | 283 | No crystals |
| 24 | 2-8° C. | 137 | 280 | No crystals |
| 72 | 2-8° C. | 138 | 293 | No crystals |

The measurements made from the formulation of Example 2 after dilution (1:8 in normal saline) are set forth in Table 13:

TABLE 13

| Time | | Particle Size (nm) | | Optical Microscopic |
|---|---|---|---|---|
| (Days) | Condition | Mean | 99 Percentile< | Observations |
| Initial | Room temp. | 147 | 305 | No crystals |
| 3 | Room temp. | 142 | 302 | No crystals |
| 4 | Room temp. | 145 | 311 | No crystals |

EXAMPLE 5

This example demonstrates the entrapment efficiency of the formulation manufactured in accordance with Example 3. The drug entrapment efficiency was determined by size exclusion column chromatography using SEPHADAX G-50 column. The drug and lipid contents were determined by HPLC methods. The entrapment efficiencies are shown in Tables 14 and 15 at room temperature and refrigerator temperature, respectively.

TABLE 14

| Time (Days) | Condition | Entrapment Efficiency (%) |
|---|---|---|
| Initial | Room temp. | >90 |
| 1 | Room temp. | >90 |
| 2 | Room temp. | >90 |
| 3 | Room temp. | >90 |

TABLE 15

| Time (Days) | Condition | Entrapment Efficiency (%) |
|---|---|---|
| Initial | Refrigerator temp. | >90 |
| 1 | Refrigerator temp. | >90 |
| 2 | Refrigerator temp. | >90 |
| 3 | Refrigerator temp. | >90 |

EXAMPLE 6

This example presents a comparative multiple IV dose toxicity study of Taxol and Liposome Encapsulated Paclitaxel (LEP).

Materials and Methods

Test System

CD2F1 mice (4-6 weeks old, Male and Female) used for the study were obtained through Harlan Sprague Dawley Laboratories. The individual animal was identified by ear tag. Upon arrival, the animals were placed in quarantine for 7 days. The animals were kept in an environmentally monitored, well-ventilated room maintained at a temperature of 64-84° F. and a relative humidity of 30%-70%. Fluorescent lighting provided illumination approximately 12hours per day. Mice were offered ad libitum 8656 HT Rodent Diet (Harlan Teklad, Madison, Wis.) during the quarantine and study periods. The average weight of mice on day 1 of study was 16-22 g (female) and 20-27 (male). The age of mice on day 1 of study was 6-7 weeks.

Test and Control Articles

Test Articles:
1. Lyophilized Liposomal Paclitaxel (LEP-ETU) vials prepared in accordance with the present invention were stored at 2-8 ° C.
2. Taxol vials (30 mg/vial; concentration 6 mg/mL) were received from Mead Johnson, Inc.

Control Article:
1. Placebo liposome was stored at 2-8 ° C.

Dose Formulations Preparation:

Vehicle formulations (LEP and Placebo liposome) were prepared fresh on each day of dosing. The stability of reconstituted and diluted formulations (up to 8 fold with 0.9% saline) is 12 hours at 20-25° C. All the dosing solutions were used within 12 hours after reconstitution and dilution.

Experimental Design

Randomization and Group Assignment

Randomization was done during week 1. Animals were weighed prior to randomization and only the animals whose weight ranged between 16-23 g (Female) and 17-26 g (Male) were used for randomization and were assigned to the following groups (7 animals/sex/group). The randomization is presented in Table 16:

TABLE 16

| Group Number | Treatment | Dose Level (mg/kg/day) | Dose Concentration (mg/mL) | Dose volume (mL/Kg/dose) |
|---|---|---|---|---|
| 1 | Placebo Liposome | 0.0 | 0.0 | 25 |
| 2 | LEP | 25.0 | 1.0 | 25 |
| 3 | LEP | 50.0 | 2.0 | 25 |
| 4. | Cremophor EL/Ethanol | 0.0 | 0.0 | 25 |
| 5. | Cremophor EL/Ethanol | 0.0 | 0.0 | 25 |
| 6 | Taxol | 12.5 | | |
| 7 | Taxol | 25.0 | | |

Article (Control and Test) Administration:

Each animal was weighed prior to dosing. Mice received control or test article intravenously via tail vein once a day for 5 consecutive days. The injection volume was based on individual mouse body weight. The control animals in Group 1 received approximately the same amount of lipids as in 50 mg/kg dose of LEP. The control animals in Groups 4 and 5 received the equivalent amount of Cremophor EL/Ethanol as in Group 6 and 7, respectively but without Paclitaxel.

Observations

Animals were weighed daily during the dosing period (Day 1-5) and thereafter three times a week for up to 22 days. Animals were observed once daily during the study period for morbidity/mortality. Animals were observed approximately 1 to 2 hours post dosing for clinical signs and daily thereafter. Detailed physical examination for toxicity was done on Day 1 and thereafter once a week.

Results

Body Weights

There was no body weight loss in animals that received placebo liposome. Female mice given IV doses of LEP (25 mg/kg/dose) lost weight by 5.2% on Day 8 and recovered completely by Day 10. There was a 12.5% body weight loss for male mice that received LEP (25 mg/kg/dose) by Day 8 and the complete recovery was achieved by Day 15. The weight loss for male and female mice in Group 3 (50 mg/kg/dose, LEP) were 20.6 and 28.7% by Day 8. The control animals that were injected with Cremophor EL/Ethanol had no body weight loss. The weight loss for females in Group 5 (12.5 mg/kg/dose, Taxol) was negligible. The male animals in Group 5 had a body weight loss of 4.7% by Day 5 and the recovery was complete by Day 12. Female animals in Group 7 (25 mg/kg/dose, Taxol) had a body weight loss of 6.3% by Day 8 and they recovered completely from body weight loss by Day 12. The weight loss for male animals in Group 7 was 10.4% on Day 8 and the recovery was complete by Day 15. The percentage of survival (Total/Number surviving) is presented in Tables 17 and 18. On Day 4, one male animal in Group 7 (25 mg/kg/dose, Taxol) died 1 hour after administration of article. One animal in Group 4 was sacrificed on Day 17 because of wounded tail.

TABLE 17

A Comparative Multiple IV Dose Toxicity Study of Taxol and LEP: Percentage of Survival of Female animals (Number surviving/Total)

| Day | Group 1 Female | Group 2 Female | Group 3 Female | Group 4 Female | Group 5 Female | Group 6 Female | Group 7 Female |
|---|---|---|---|---|---|---|---|
| 1 | 100(7/7) | 100(7/7) | 100(7/7) | 100(7/7) | 100(7/7) | 100(7/7) | 100(7/7) |
| 2 | 100(7/7) | 100(7/7) | 100(7/7) | 100(7/7) | 100(7/7) | 100(7/7) | 100(7/7) |
| 3 | 100(7/7) | 100(7/7) | 100(7/7) | 100(7/7) | 100(7/7) | 100(7/7) | 100(7/7) |
| 4 | 100(7/7) | 100(7/7) | 100(7/7) | 100(7/7) | 100(7/7) | 100(7/7) | 100(7/7) |
| 5 | 100(7/7) | 100(7/7) | 100(7/7) | 100(7/7) | 100(7/7) | 100(7/7) | 100(7/7) |
| 6 | 100(7/7) | 100(7/7) | 100(7/7) | 100(7/7) | 100(7/7) | 100(7/7) | 100(7/7) |
| 7 | 100(7/7) | 100(7/7) | 100(7/7) | 100(7/7) | 100(7/7) | 100(7/7) | 100(7/7) |
| 8 | 100(7/7) | 100(7/7) | 100(7/7) | 100(7/7) | 100(7/7) | 100(7/7) | 100(7/7) |

TABLE 17-continued

A Comparative Multiple IV Dose Toxicity Study of Taxol and LEP: Percentage of Survival of Female animals (Number surviving/Total)

| Day | Group 1 Female | Group 2 Female | Group 3 Female | Group 4 Female | Group 5 Female | Group 6 Female | Group 7 Female |
|---|---|---|---|---|---|---|---|
| 9  | 100(7/7) | 100(7/7) | 0(7/7) | 100(7/7) | 100(7/7) | 100(7/7) | 100(7/7) |
| 10 | 100(7/7) | 100(7/7) | 0(7/7) | 100(7/7) | 100(7/7) | 100(7/7) | 100(7/7) |
| 11 | 100(7/7) | 100(7/7) | 0(7/7) | 100(7/7) | 100(7/7) | 100(7/7) | 100(7/7) |
| 12 | 100(7/7) | 100(7/7) | 0(7/7) | 100(7/7) | 100(7/7) | 100(7/7) | 100(7/7) |
| 13 | 100(7/7) | 100(7/7) | 0(7/7) | 100(7/7) | 100(7/7) | 100(7/7) | 100(7/7) |
| 14 | 100(7/7) | 100(7/7) | 0(7/7) | 100(7/7) | 100(7/7) | 100(7/7) | 100(7/7) |
| 15 | 100(7/7) | 100(7/7) | 0(7/7) | 100(7/7) | 100(7/7) | 100(7/7) | 100(7/7) |
| 16 | 100(7/7) | 100(7/7) | 0(7/7) | 100(7/7) | 100(7/7) | 100(7/7) | 100(7/7) |
| 17 | 100(7/7) | 100(7/7) | 0(7/7) | 100(7/7) | 100(7/7) | 100(7/7) | 100(7/7) |
| 18 | 100(7/7) | 100(7/7) | 0(7/7) | 100(7/7) | 100(7/7) | 100(7/7) | 100(7/7) |
| 19 | 100(7/7) | 100(7/7) | 0(7/7) | 100(7/7) | 100(7/7) | 100(7/7) | 100(7/7) |
| 20 | 100(7/7) | 100(7/7) | 0(7/7) | 100(7/7) | 100(7/7) | 100(7/7) | 100(7/7) |
| 21 | 100(7/7) | 100(7/7) | 0(7/7) | 100(7/7) | 100(7/7) | 100(7/7) | 100(7/7) |
| 22 | 100(7/7) | 100(7/7) | 0(7/7) | 100(7/7) | 100(7/7) | 100(7/7) | 100(7/7) |

Group 1: Placebo liposome equivalent to lipid amount present in the LEP dose of 50 mg/kg;
Group 2: LEP 25 mg/kg;
Group 3: LEP 50 mg/kg;
Group 4: Cremophor EL/Ethanol equivalent to cremophor EL/Ethanol present in Taxol dose of 12.5 mg/kg;
Group 5: Cremophor EL/Ethanol equivalent to cremophor EL/Ethanol present in Taxol dose of 25 mg/kg;
Group 6: Taxol 12.5 mg/kg;
Group 7: Taxol 25 mg/kg.

TABLE 18

A Comparative Multiple IV Dose Toxicity Study of Taxol and LEP: Percentage of Survival of Male animals (Number surviving/Total)

| Day | Group 1 Male | Group 2 Male | Group 3 Male | Group 4 Male | Group 5 Male | Group 6 Male | Group 7 Male |
|---|---|---|---|---|---|---|---|
| 1  | 100(7/7) | 100(7/7) | 100(7/7) | 100(7/7) | 100(7/7) | 100(7/7) | 100(7/7) |
| 2  | 100(7/7) | 100(7/7) | 100(7/7) | 100(7/7) | 100(7/7) | 100(7/7) | 100(7/7) |
| 3  | 100(7/7) | 100(7/7) | 100(7/7) | 100(7/7) | 100(7/7) | 100(7/7) | 100(7/7) |
| 4  | 100(7/7) | 100(7/7) | 100(7/7) | 100(7/7) | 100(7/7) | 100(7/7) | 86(6/7) |
| 5  | 100(7/7) | 100(7/7) | 86(6/7) | 100(7/7) | 100(7/7) | 100(7/7) | 86(6/7) |
| 6  | 100(7/7) | 100(7/7) | 71.4(5/7) | 100(7/7) | 100(7/7) | 100(7/7) | 86(6/7) |
| 7  | 100(7/7) | 100(7/7) | 57.1(4/7) | 100(7/7) | 100(7/7) | 100(7/7) | 71(5/7) |
| 8  | 100(7/7) | 100(7/7) | 0(7/7) | 100(7/7) | 100(7/7) | 100(7/7) | 71(5/7) |
| 9  | 100(7/7) | 100(7/7) | 0(7/7) | 100(7/7) | 100(7/7) | 100(7/7) | 57(4/7) |
| 10 | 100(7/7) | 100(7/7) | 0(7/7) | 100(7/7) | 100(7/7) | 100(7/7) | 57(4/7) |
| 11 | 100(7/7) | 100(7/7) | 0(7/7) | 100(7/7) | 100(7/7) | 100(7/7) | 57(4/7) |
| 12 | 100(7/7) | 100(7/7) | 0(7/7) | 100(7/7) | 100(7/7) | 100(7/7) | 57(4/7) |
| 13 | 100(7/7) | 100(7/7) | 0(7/7) | 100(7/7) | 100(7/7) | 100(7/7) | 57(4/7) |
| 14 | 100(7/7) | 100(7/7) | 0(7/7) | 100(7/7) | 100(7/7) | 100(7/7) | 57(4/7) |
| 15 | 100(7/7) | 100(7/7) | 0(7/7) | 100(7/7) | 100(7/7) | 100(7/7) | 57(4/7) |
| 16 | 100(7/7) | 100(7/7) | 0(7/7) | 100(7/7) | 100(7/7) | 100(7/7) | 57(4/7) |
| 17 | 100(7/7) | 100(7/7) | 0(7/7) | 86(6/7) | 100(7/7) | 100(7/7) | 57(4/7) |
| 18 | 100(7/7) | 100(7/7) | 0(7/7) | 86(6/7) | 100(7/7) | 100(7/7) | 57(4/7) |
| 19 | 100(7/7) | 100(7/7) | 0(7/7) | 86(6/7) | 100(7/7) | 100(7/7) | 57(4/7) |
| 20 | 100(7/7) | 100(7/7) | 0(7/7) | 86(6/7) | 100(7/7) | 100(7/7) | 57(4/7) |
| 21 | 100(7/7) | 100(7/7) | 0(7/7) | 86(6/7) | 100(7/7) | 100(7/7) | 57(4/7) |
| 22 | 100(7/7) | 100(7/7) | 0(7/7) | 86(6/7) | 100(7/7) | 100(7/7) | 57(4/7) |

Group 1: Placebo liposome equivalent to lipid amount present in the LEP dose of 50 mg/kg;
Group 2: LEP 25 mg/kg;
Group 3: LEP 50 mg/kg;
Group 4: C remophor EL/Ethanol equivalent to cremophor EL/Ethanol present in Taxol dose of 12.5 mg/kg;
Group 5: Cremophor EL/Ethanol equivalent to cremophor EL/Ethanol present in Taxol dose of 25 mg/kg;
Group 6: Taxol 12.5 mg/kg;
Group 7: Taxol 25 mg/kg.

Clinical Signs of Toxicity

Clinical signs of toxicity of animals in each group on various days is presented in Table 19. Clinical signs of toxicity as manifested by hunched posture and rough coats were observed in animals in Group 7 (25 mg/kg/dose, Taxol) starting from Day 4. Starting from Day 9 till Day 15, the animals in Group 7 showed neurological signs of toxicity manifested by problems in walking and dragging the back legs towards abdomen. On Day 6, four male animals in Group 6 (12.5 mg/kg/dose, Taxol) had rough coats and three were dehydrated but by Day 7, they appeared to be normal. Animals in Group 3 (50 mg/kg/dose LEP), had severe signs of toxicity as manifested by hunched posture, dehydration and rough coats between Day 6-9 and the animals in this group were either dead or moribund sacrificed by Day 9.

Clinical Observations

The detailed physical for toxicity was done on Days 1, 10, 17, and 22 and is presented in Table 20.

Unscheduled Observations

All the animals in Group 5 receiving a dose of Cremophor EL/Ethanol equivalent to that present in 25 mg/kg/dose of Taxol and Group 7 (25 mg/kg/dose, Taxol) had decreased activity after dosing. All the unscheduled observations after dosing are presented in a tabular form (Table 21).

Conclusions

The tolerated dose for LEP was 25 mg/kg/day (once daily×5 days, whereas for Taxol, a dose of 12.5 mg/kg/day (once daily×5 days) could be administered safely to CD2F1 mice.

TABLE 19

A Comparative Multiple IV dose Toxicity Study of Taxol (Paclitaxel) and LEP in CD2F1 mice: Animal Clinical Signs for Toxicity on Different Days

| Day (s) | Clinical Signs |
|---|---|
| 1-2 | Animals in all groups were normal. |
| 3 | Animals in Groups 1-6 were normal. All animals in Group 7 had rough coats and hunched posture. |
| 4 | Animals in Group 1-6 were normal. Animals in Group 7 had rough coats and hunched posture. |
| 5 | Animals in Groups 1-6 were normal. All animals in Group 7 had rough coats. |
| 6 | All animals in Group 1 were normal. Four female animals in Group 2 (ID# 16, 17, 37, 45) were dehydrated and had rough coats. One female animal in Group 2 (ID# 38) had a rough coat. Six male animals in Group 2 (ID# 76, 77, 133, 134, 90, 125) were dehydrated and had rough coats. One male animal in Group 2 (ID# 128) was dehydrated. Three females in Group 3 (ID# 23, 24, and 31) had rough coats, piloerection, hunched posture, and were dehydrated. Four females in Group 3 (ID# 33, 3, 4, and 10) had hunched posture, piloerection and were dehydrated. Two males in Group 3 (ID# 110 and 119) had rough coats, hunched posture and were dehydrated. Two males in Group 3 (ID# 85 and 127) had rough coats, piloerection, hunched posture and were dehydrated. One male in Group 3 (ID# 108) had a rough coat, hunched posture, piloerection, swollen tongue, and was dehydrated. One male in Group 3 (ID# 118) had a rough coat, hunched posture, swollen tongue, swollen eye, and was dehydrated. All females in Group 4 were normal. All males in Group 4 were normal, except (ID# 100) which had a scab on its tail. All animals in Group 5 were normal except one male animal (ID# 99) which had a rough coat. All females in Group 6 and three males in Group 6 (ID# 86, 98, and 124) were normal. Three males in Group 6 (ID# 79, 93, and 137) were dehydrated and had rough coats. One male animal in Group 6 (ID#96) was dehydrated. Except one animal (ID#11 who was normal), all females in Group 7 were dehydrated. All male animals in Group 7 were dehydrated and had rough coats. Five male animals in Group 7 (ID# 81, 88, 116, 131, and 142) had hunched posture. Four male animals in Group 7 (ID# 81, 88, 131, 142) appeared to have lump in the upper, left abdominal area. |
| 7 | All animals in Groups 1, 2, 4, 5 and 6 were normal. All female animals in Group 3 had decreased activity, and rough coats. All male animals in Group 3 had decreased activity. All female animals in Group 7 were normal. All male animals in Group 7 had rough coats. |
| 8 | All animals in Groups 1, 2, 5 and 6 were normal. All females in Groups 4 and 7 were normal. All female animals in Group 3 had rough coats and hunched posture. All males in Group 3 were dehydrated, had rough coats, hunched posture and decreased activity. All male animals in Group 4 were normal except one male (ID#100) had an open wound on its tail. All male animals in Group 7 had rough coats. |
| 9 | All animals in Groups 1, 2, 5 and 6 were normal. All females in Groups 4 and 7 were normal. All female animals in Group 3 had rough coats and hunched posture. Three female animals in Group 3 (ID# 23, 24, 31) were also dehydrated. Two female animals in Group 3 (ID# 3, 4) had lameness in the back and front legs. One animal in Group 3 (ID# 10) had lameness in the back legs. All male animals in Group 4 were normal except one male (ID# 100) had a damaged tail. All male animals in Group 7 had rough coats. One male animal in Group 7 (ID# 142) was also dehydrated, had hunched posture and lameness in the back legs. |
| 10 | All animals in Groups 1, 2, 5 and 6 were normal. All female animals in Group 4 were normal. One male animal in Group 4 (ID# 100) had a damaged tail, all other males in this group were normal. All animals in Group 7 were ataxic. |
| 11 | All animals in Groups 1, 2, 5 and 6 were normal. All female animals in Group 4 were normal. All male animals in Group 4 were normal except one male animal (ID# 100) had damaged tail. All female animals in Group 7 had piloerection. All male animals in Group 7 had piloerection, except one male animal (ID# 113) had a rough coat. |
| 12 | All animals in Group 1 were normal. All female animals in Groups 2, 4 and 6 were normal. All male animals in Group 2 were dehydrated. Six male animals in Group 2 (ID# 76, 77, 133, 134, 90, and 125) were ataxic. Six male animals in Group 4 (ID# 122, 135, 114, 100, 112, and 129) were dehydrated. Three male animals in Group 4 (ID# 100, 112, 129) had rough coats. One male animal in Group 4 (ID# 100) had a damaged tail. All females in Group 5 were normal, except one animal (ID# 13) was dehydrated. One male animal in Group 5 (ID# 120) was normal. Six male animals in Group 5 (ID# 87, 89, 123, |

TABLE 19-continued

A Comparative Multiple IV dose Toxicity Study of Taxol (Paclitaxel) and LEP in CD2F1 mice: Animal Clinical Signs for Toxicity on Different Days

| Day(s) | Clinical Signs |
|---|---|
|  | 80, 99, and 136) were dehydrated. One male in Group 5 (ID# 80) had a rough coat. All male animals in Group 6 were normal, except two male animals (ID# 86, 79) were dehydrated. All animals in Group 7 were ataxic. Two female animals in Group 7 (ID# 49 and 47), and all males in Group 7 were also dehydrated. |
| 13 | All animals in Groups 1, 2, 5 and 6 were normal. All female animals in Group 4 were normal. All males in Group 4 were normal, except one male animal (ID# 100) had a damaged tail. The animal # 100 had damaged tail. All animals in Group 7 were ataxic. |
| 14 | All animals in Groups 1, 2, 5 and 6 were normal. All female animals in Group 4 and 7 were normal. Two male animals in Group 4 (ID# 100 and 129) had rough coats. All male animals in Group 7 were ataxic. Three male animals in Group 7 (ID# 81, 116, and 113) were dehydrated. One male animal in Group 7 (ID# 113) had a rough coat. |
| 15 | All animals in Groups 1, 2, 5 and 6 were normal. All female animals in Group 4 and 7 were normal. One male animal in Group 4 (ID# 100) had a damaged tail. All male animals in Group 7 were ataxic. |
| 16 | All animals in Groups 1, 2, 5, and 6 were normal. All female animals in Groups 4 and 7 were normal. One male animal in Group 4 (ID# 100) had a damaged tail. All male animals in Group 7 were ataxic. |
| 17 | All animals in Groups 1, 2, 5, 6, and 7 were normal. All female and male animals in Group 4 were normal, except one male animal (ID# 100) had a severely damaged tail. |
| 18-21 | Animals in all Groups were normal. |
| 22 | Animals in Groups 1, 2 and 7 were normal. All female animals in Groups 4, 5, and 6 were normal. One male animal in Group 4 (ID# 129), two male animals in Group 5 (ID# 123, 136) and one male in Group 6 (ID# 79) were dehydrated. |

Group 1: Placebo liposome equivalent to lipid amount present in the LEP dose of 50 mg/kg;
Group 2: LEP 25 mg/kg;
Group 3: LEP 50 mg/kg;
Group 4: Cremophor EL/Ethanol equivalent to cremophor EL/Ethanol present in Taxol dose of 12.5 mg/kg;
Group 5: Cremophor EL/Ethanol equivalent to cremophor EL/Ethanol present in Taxol dose of 25 mg/kg;
Group 6: Taxol 12.5 mg/kg;
Group 7: Taxol 25 mg/kg.

TABLE 20

A Comparative Multiple IV dose Toxicity Study of Taxol (Paclitaxel) and LEP in CD2F1 mice: Clinical observations

| Day(s) | Clinical Observations |
|---|---|
| 1 | Animals in all groups were normal. |
| 10 | All animals in Groups 1 and 5 were normal. Three female animals in Group 2 (ID# 14, 15 and 16) were normal. Three female animals in Group 2 (ID# 17, 37 and 45) had lumps in the upper left abdominal area. One female animal in Group 2 (LD# 38) was ataxic. All male animals in Group 2 were normal, except one male animal (ID# 125) had a lump in the upper left abdominal area. Six female animals in Group 4 (ID# 2, 9, 44, 22, 25 and 46) were normal. One female animal in Group 4 (ID# 32) had lump in the upper left abdominal area. Six male animals in Group 4 (ID# 122, 126, 135, 114, 112 and 129) were normal. One male animal in Group 4 (ID# 100) had severely damaged tail. Five female animals in Group 6 (ID# 27, 42, 20, 21 and 41) were normal. One female animal in Group 6 (ID# 12) had a lump in the upper left abdominal area. One female animal in Group 6 (ID#40) was dehydrated. All male animals in Group 6 were normal, except two male animals (ID# 124 and 79) were dehydrated. All animals in Group 7 were ataxic and dehydrated. Two female animals (ID# 28, 30) and one male animal (ID# 113) in Group 7, had lump in the upper left abdominal area. Three male animals in Group 7 (ID# 88, 116 and 113) had rough coats. One male animal in Group 7 (ID#88) had hunched posture. |
| 17 | All animals in Groups 1 and 2 were normal. All female and male animals in Group 4 were normal, except one male animal (ID# 100) had a necrotic tail. All female animals in Group 5 were normal. Four male animals in Group 5 (ID# 87, 120, 123 and 136) were dehydrated. Three male animals in Group 5 (ID# 89, 80 and 99) were normal. All animals in Group 6 were normal, except one male animal (ID#79) was dehydrated. All female animals in Group 7 were normal. Three male animals in Group 7 (ID# 81, 88 and 113) had uncoordinated movements in left hind leg. Three male animals in Group 7 (ID# 88, 116 and 113) were dehydrated. |

TABLE 20-continued

A Comparative Multiple IV dose Toxicity Study of Taxol (Paclitaxel) and LEP in CD2F1 mice: Clinical observations

| Day (s) | Clinical Observations |
|---|---|
| 22 | Animals in Groups 1, 2 and 7 were normal. All animals in Group 4 were normal, except one male animal (ID# 129) was dehydrated. All animals in Group 5 were normal except two male animals (ID#123 and 136) were dehydrated. All animals in Group 6 were normal, except one male animal (ID# 79) was dehydrated. |

Group 1: Placebo liposome equivalent to lipid amount present in the LEP dose of 50 mg/kg;
Group 2: LEP 25 mg/kg; Group 3: LEP 50 mg/kg;
Group 4: Cremophor EL/Ethanol equivalent to cremophor EL/Ethanol present in Taxol dose of 12.5 mg/kg;
Group 5: Cremophor EL/Ethanol equivalent to cremophor EL/Ethanol present in Taxol dose of 25 mg/kg;
Group 6: Taxol 12.5 mg/kg; Group 7: Taxol 25 mg/kg.

TABLE 21

A comparative multiple IV dose toxicity study of LEP and Taxol: Unscheduled observations: Unscheduled Observations

| Day | Unscheduled Observations |
|---|---|
| 1 | All animals in Groups 5 and 7 were comatose after dosing. One female animal in Group 6 (ID#20) had decreased activity after dosing. |
| 2 | All animals in Groups 5 and 7 and one animal in Group 7 (ID# 137) were comatose after dosing. |
| 3 | All animals in Groups 6 and 7 appeared to have decreased activity after dosing. One male animal (#83) and one female animal (#1) in Group 1 had scab on tail. |
| 4 | All animals in Groups 6 and 7 appeared to have decreased activity after dosing. One male animal in Group 3 (ID#85) had a wound on its tail. One male in Group 4 (ID#100) had multiple wounds on its tail. Two male animals (ID# 83 and 117) appeared to have a scab on their tails. One male animal in Group 1 (ID#132) had tail sheet coming off the base of its tail. |
| 5 | One male animal in Group 1(ID#130) died after dosing. One male animal in Group 2 (ID#125) had multiple wounds on its tail. One male animal in Group 1 (ID#132) had a scab on its tail. |

Group 1: Placebo liposome equivalent to lipid amount present in the LEP dose of 50 mg/kg;
Group 2: LEP 25 mg/kg;
Group 3: LEP 50 mg/kg;
Group 4: Cremophor EL/Ethanol equivalent to cremophor EL/Ethanol present in Taxol dose of 12.5 mg/kg;
Group 5: Cremophor EL/Ethanol equivalent to cremophor EL/Ethanol present in Taxol dose of 25 mg/kg;
Group 6: Taxol 12.5 mg/kg;
Group 7: Taxol 25 mg/kg.

EXAMPLE 7

This example presents the results of a Therapeutic efficacy evaluation of liposome based formulation taxol (LEP) in SCID mice bearing human lung tumor (A549).

Materials and Methods

Cell Line and Culture Condition:

The lung adenocarcinoma cell line A-549 was obtained from the American Type Culture Collection (Rockville, Md.) and maintained in RPMI-1640 medium (Life Technologies Inc., Grand island, N.Y.) supplemented with 10% heat inactivated fetal bovine serum (Life Technologies Inc., Grand island, N.Y.). The cell line was grown at 37° C. in a humidified 5% $CO_2$ incubator.

Mice:

C.B.-17 SCID female mice (3-4 weeks old) were received from Harlan Sprague Dawley (Indianapolis, Ind.). Mice were handled aseptically and housed in a micro isolator in accordance with standard operating procedures (SOPs) of NeoPharm Research and Development, and received sterile food and water ad libitum. Mice were acclimated for at least five days before initiating the study.

Drug and Formulation:

Taxol was obtained from MeadJohonson (Lot #IL5302). Liposome entrapped taxol and blank liposome were obtained as described above.

Tumor Transplantation:

Logarithmically grown A549 cells suspension 50×106/mL was prepared and mice were transplanted with 5×106 cells (0.1 mL) subcutaneously at the left flank region (6). Tumor growth was measured with digital caliper (Mitutoyo Corporation, Japan) and tumor volume was determined by using formula: [length×(width/2) 2×p].

Experimental Design:

After appropriate growth of tumors (23 days) animals were randomly divided into different treatment groups (5-7 animals/group) and treated with LEP (12.5 or 25 50 mg/kg×3) or taxol (12.5 or 25.0 mg/kg×3) or blank liposome or cremophor-EL on day 1, 4, and 8. Tumor growth inhibition was monitored till day 28 of post treatment.

Results and Discussion:

Antitumor efficacy was evaluated in established human lung tumor xenograft model implanted subcutaneously in SCID mice. The efficacy of LEP and taxol was determined in multiple dose intravenous injection on day 1,4 and 8. Animal groups treated with taxol at 12.5 and 25.0 mg/kg resulted in a 37% and 57% inhibition of tumor growth, respectively, compared to blank liposome treated groups.(FIG. 1). However, inhibition of tumor growth was much more pronounced in animal groups treated with LEP. LEP treatment at 12.5, 25.0 and 50 mg/kg resulted in 44%, 85% and 95% tumor growth inhibition, respectively, compared to the control group.

Figure 2:
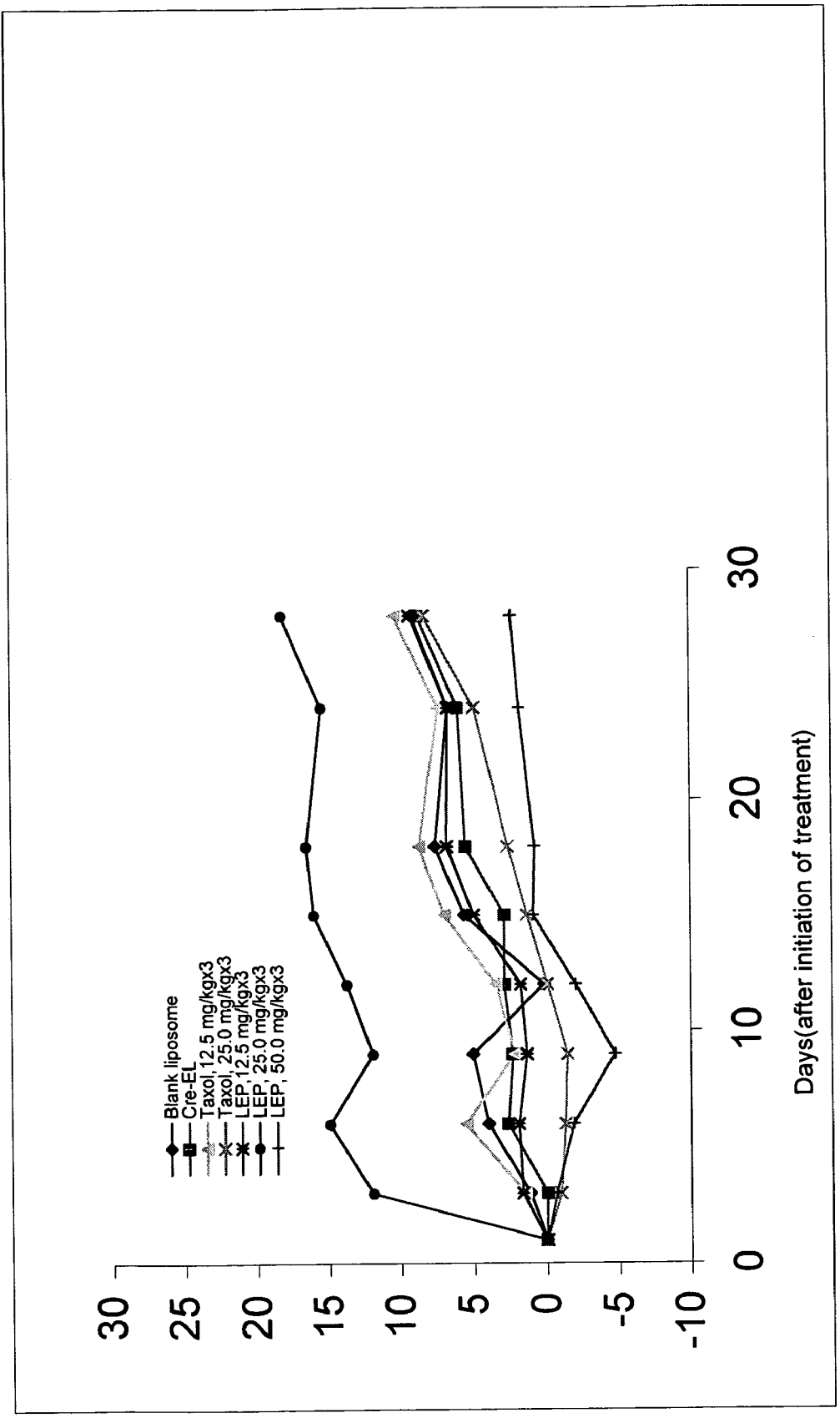
FIG. 2 graphically presents the results of a study of the effect of liposome entrapped paclitaxel (LEP) and Taxol on body weight of human lung tumor bearing SCID mice.

Both LEP and taxol were well tolerated at all the doses tested as judged by body weight loss (FIG. 2). Only less than 5% body weight loss was noticed in case of LEP 50 mg/kg treated animal group.

Higher tumor growth inhibition of LEP treated animals could be due to the optimal availability of taxol at target site for longer period of time. Liposome based formulation of taxol has two advantages. Firstly, it helps to deliver the drug without using any surfactants. In addition, it provides sustained levels of drug for longer periods of time, which thus provides for greater antitumor effects.

All of the references cited herein, including patents, patent applications, and publications, are hereby incorporated in their entireties (SP) by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

We claim:

1. A formulation of paclitaxel encapsulated in a liposome, wherein the liposome comprises a lipid fraction, and the lipid fraction comprises 1,2-dioleoyl-sn-glycero-3-phosphocholine (DOPC), tetramyristoyl cardiolipin (CL) and cholesterol (CH), wherein the DOPC comprises between about 90 percent to about 92 percent of the lipid fraction, wherein the amount of the lipid fraction is at least about 3.5% w/v of the formulation and not more than about 8.5% w/v of the formulation, and wherein the liposomes have a mean size of 50 to 200 nm, and wherein said formulation is stable in an aqueous solution at room temperature for at least three days.

2. The formulation of claim 1, wherein the concentration of CH is between about 1 mg/ml and about 2 mg/ml, the concentration of CL is between about 2 mg/ml and about 8 mg/ml; and the concentration of DOPC is between about 44 mg/ml and about 74 mg/ml of the formulation.

3. The formulation of claim 1, wherein the paclitaxel is selected from a group consisting of 7-epipaclitaxel, t-acetyl paclitaxel, 10-desacetyl-paclitaxel, 10- desacetyl-7-epipaclitaxel, 7-xylosylpaclitaxel, 10-desacetyl-7-glutarylpaclitaxel, 7-N-N-dimethylglycylpaclitaxel, 7-L-alanylpaclitaxel and mixtures thereof.

4. The formulation of claim 1, wherein the formulation does not contain visible paclitaxel drug crystal or precipitate, as confirmed by microscopic examination.

5. The formulation of claim 1, wherein the formulation is free of paclitaxel drug crystal and precipitate.

6. The formulation of claim 1, wherein at least 75 percent of the paclitaxel is encapsulated in the liposome.

7. The formulation of claim 1, wherein at least 85 percent of the paclitaxel is encapsulated in the liposome.

8. The formulation of claim 1, wherein at least 90 percent of the paclitaxel is encapsulated in the liposome.

9. The formulation of claim 1, wherein the ratio of lipid fraction to the paclitaxel is between about 10:1 and about 70:1 by molar ratio.

10. The formulation of claim 1, further comprising D-alpha tocopherol acid succinate.

11. The formulation of claim 1, further comprising a lyoprotectant.

12. The formulation of claim 11, wherein the lyoprotectant comprises one or more sugars selected from a group consisting of sucrose, mannitol, trehalose, maltose, lactose, glucose, dextran, aminoglycosides, streptomycin and combinations thereof.

13. The formulation of claim 1, wherein the liposomes have been sterile-filtered.

14. The formulation of claim 13, wherein the liposomes have been sterile-filtered through a 0.22 micron filter.

15. The formulation of claim 1, wherein the liposomes have a mean size of 100-180 nm.

16. The formulation of claim 1, wherein the liposomes have a mean size of 120-160 nm.

17. The formulation of claim 1, wherein the liposomes are in a lyophilized form.

18. A method of making the formulation of claim 1, comprising dissolving 2-dioleoyl-sn-glycero-3-phosphocholine (DOPC), tetramyristoyl cardiolipin (CL), cholesterol (CH) and the paclitaxel in an organic solvent, wherein the DOPC comprises between about 90 percent to about 92 percent of the lipid fraction.

19. The method of claim 18, wherein the DOPC, CH and CL has a molar ratio of DOPC:CH:CL of between about 92:0:8 and about 90:5:5.

20. The method of claim 18, wherein the organic solvent is selected from a group consisting of methylene chloride, ethanol, methyl acetate and ethyl formate.

21. The method of claim 18, further comprising an, antioxidant.

22. The method of claim 18, further comprising substantially removing the organic solvent to form a dried lipid residue.

23. The method of claim 18, further comprising hydrating the lipid residue with an aqueous solution to form liposomes.

24. The method of claim 23, wherein the hydration further comprises mixing the lipid residue with the aqueous solution to form liposomes.

25. The method of claim 18, further comprising adding a lyoprotectant.

26. The metliod of claim 25, wherein the lyoprotectant is selected from a group consisting of sucrose, mannitol, trehalose, maltose, lactose, glucose, dextran, aminoglycosides, streptomycin and combinations thereof.

27. The method of claim 18, further comprising adding a tonicity adjuster.

28. The method of claim 23, further comprising sterile filtering the liposomes.

29. The method of claim 28, wherein the filtering is through a 0.22 micron filter.

30. The method of claim 23, further comprising lyophilizing the liposomes.

31. The method of claim 23, further comprising reconstituting the liposomes in a polar solvent.

32. A method of administering the formulation of claim 1, the method comprising administering to a human patient said formulation over a period of about 90 minutes to about 180 minutes, wherein said formulation comprises from about 325 $mg/m^2$ to about 375 $mg/m^2$ of paclitaxel.

33. The method of claim 32 wherein said paclitaxel is selected from the group consisting of paclitaxel, 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, taxotere and mixtures thereof.

34. The method of claim 32 wherein said formulation further comprises a tocopherol.

35. The method of claim 32 wherein said formulation comprises 325 mg/m$^2$ of paclitaxel.

36. The method of claim 32 wherein said formulation is administered by intravenous infusion.

37. The method of claim 32 wherein said formulation is administered over a period of about 90 minutes.

38. The method of claim 32 wherein the patient is suffering from cancer.

39. The method of claim 38 wherein said cancer is selected from the group consisting of breast, ovary and colon.

* * * * *